United States Patent
Doan

(10) Patent No.: US 6,505,401 B1
(45) Date of Patent: Jan. 14, 2003

(54) METHOD OF MAKING AN IMPLANTABLE MEDICAL ELECTRICAL LEAD

(75) Inventor: Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 163 days.

(21) Appl. No.: 09/699,161

(22) Filed: Oct. 27, 2000

Related U.S. Application Data

(62) Division of application No. 09/208,234, filed on Dec. 9, 1998, now Pat. No. 6,181,971.

(51) Int. Cl.[7] .............................................. H01R 43/02
(52) U.S. Cl. ............................. 29/860; 29/825; 29/857; 607/116; 607/122; 174/96; 174/100; 174/DIG. 8
(58) Field of Search ......................... 29/825, 857, 860, 29/867; 174/96, 97, 98, 99, 100, 135, DIG. 8; 600/372, 373, 374, 375, 377; 607/118, 119, 122

(56) References Cited

U.S. PATENT DOCUMENTS

| | | | | |
|---|---|---|---|---|
| 3,769,984 A | * | 11/1973 | Muench | 607/122 |
| 4,522,212 A | | 6/1985 | Gelinas et al. | 128/642 |
| 4,777,955 A | | 10/1988 | Brayton et al. | 128/642 |
| 5,251,643 A | | 10/1993 | Osypka | 607/122 |
| 5,330,522 A | * | 7/1994 | Kreyenhagen | 607/122 |
| 5,409,652 A | | 4/1995 | Carter | 264/105 |
| 5,458,629 A | * | 10/1995 | Baudino et al. | 607/116 |
| 5,499,981 A | | 3/1996 | Kordis | 606/41 |
| 5,524,337 A | * | 6/1996 | Houser et al. | 156/86 |
| 5,591,142 A | | 1/1997 | Van Erp | 604/282 |
| 5,632,274 A | | 5/1997 | Quedens et al. | 128/642 |
| 5,676,694 A | | 10/1997 | Boser et al. | 607/122 |

* cited by examiner

*Primary Examiner*—Rick Chang

(57) ABSTRACT

An implantable medical electrical lead is made by forming a generally radially directed bore extending between each lumen of an elongated lead body having a plurality of internal longitudinally extending, circumferentially spaced lumina, the bores being located at longitudinally and circumferentially spaced locations, then drawing an elongated conductor cable into and through each lumen of the lead body such that a terminal end thereof projects through and beyond an associated one of the bores. A metallic tube is slidably attached onto each conductor cable adjacent the cable's terminal end, then is firmly joined to its associated conductor cable. Thereupon, each metallic tube is affixed, as by welding, preferably, by laser welding, to an associated one of a plurality of tubular electrodes coaxial with, and overlying, the lead body at longitudinally spaced locations. In one instance, the tubular electrode may be a ring electrode with the lead body connected to a pacemaker. In another instance, the tubular electrode may be a shock coil electrode with the lead body connected to a defibrillator.

3 Claims, 3 Drawing Sheets

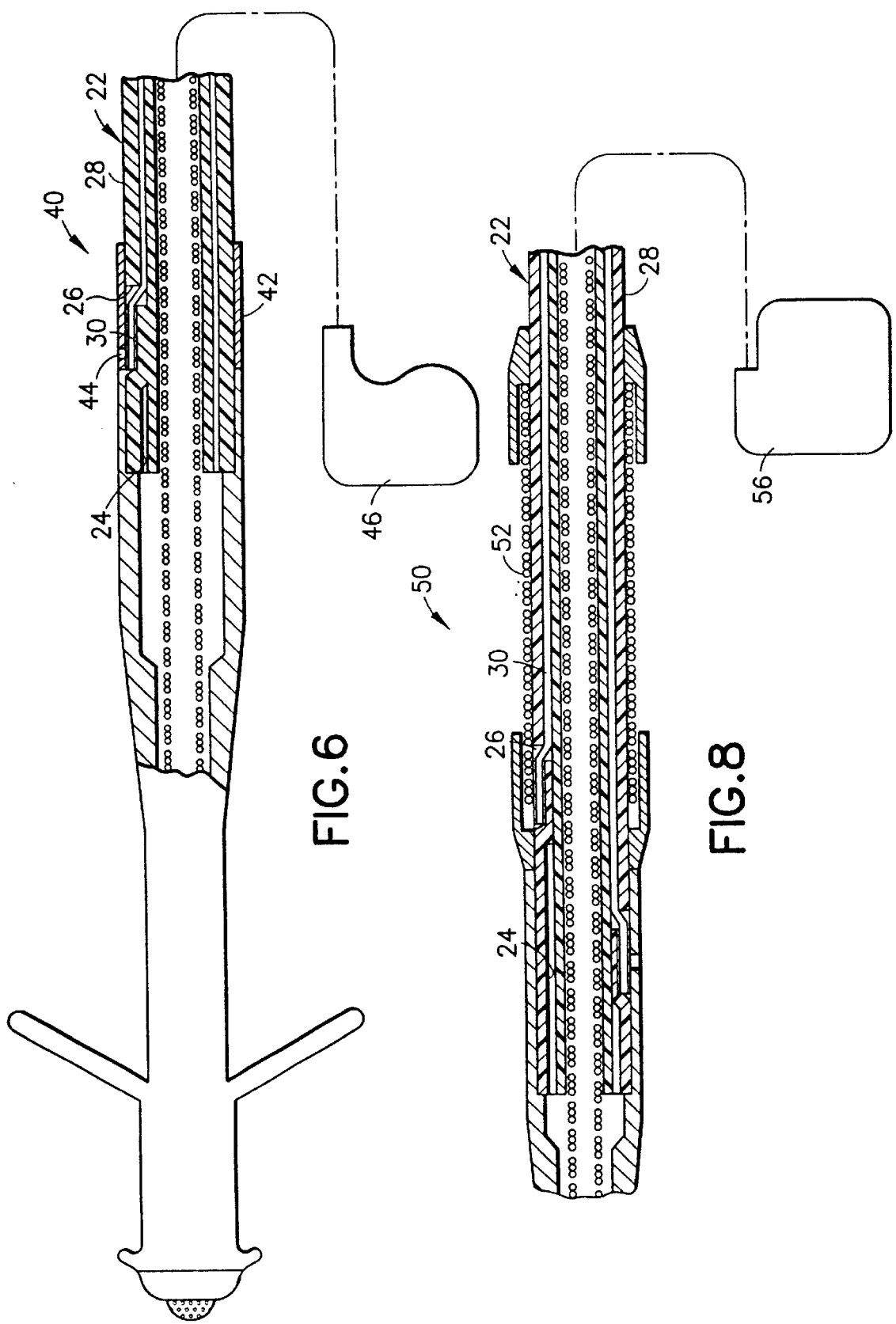

METHOD OF MAKING AN IMPLANTABLE MEDICAL ELECTRICAL LEAD

This application is a division of Ser. No. 09/208,234 filed on Dec. 9, 1998 now U.S. Pat. No. 6,181,971.

FIELD OF THE INVENTION

The present invention relates generally to electrical leads for connecting implantable medical devices with selected body tissue to be stimulated by such devices, and more particularly to techniques for providing a secure electrical and mechanical connection between an elongated conductor cable and a mating electrode.

BACKGROUND OF THE INVENTION

It has been known that implantable defibrillation leads, especially transvenous leads, typically employ elongated coils as electrodes. These electrode coils are coupled at one or both ends to an elongated conductor extending through the lead body to the electrode. Transvenous pacing leads, cardiac ablation catheters and other electrode bearing leads and catheters may also employ coil electrodes. Over the years, quite a large number of different mechanisms for interconnecting coil electrodes and conductors have been proposed including welding, crimping, and swaging. It is desirable that such connections between the conductor and the electrode provide a highly reliable electrical connection, with good mechanical properties including high tensile strength. It is also desirable that such connections allow for the lead assembly itself to retain a high degree of tensile strength through the area of the electrode:

Typically, conductors in commercially marketed pacing and defibrillation leads have taken the form of single or multifilar wire coils. However, there has been a high level of interest recent in pacing and defibrillation leads employing stranded wire conductors such as cables, instead of coiled wire conductors. Such stranded conductors present a new set of requirements for interconnection with electrode coils, if the above described design goals are to be accomplished. The present invention relates to this more recent lead technology.

Typical of the prior art in this regard is U.S. Pat. No. 5,591,142 to Van Erp which discloses encasing wires within a metal sleeve and U.S. Pat. No. 5,676,694 to Boser et al. which discloses laser welding an electrode to a sleeve and covering the electrode with a polymeric sleeve.

Other patents, as follows, disclose positioning wires outside of a conductor with subsequent mounting thereon of an electrode or the like:

| U.S. Pat. No. | Inventor(s) | Issued |
| --- | --- | --- |
| 5,632,274 | Quedens et al. | 05/27/97 |
| 5,499,981 | Kordis | 03/19/96 |
| 5,409,652 | Carter | 04/25/95 |
| 5,251,643 | Osypka | 10/12/93 |
| 4,777,955 | Brayton et al. | 10/18/88 |
| 4,522,212 | Gelinas et al. | 06/11/85 |

It was with knowledge of the foregoing state of the technology that the present invention has been conceived and is now reduced to practice.

SUMMARY OF THE INVENTION

The present invention relates to an implantable medical electrical lead made by forming a generally radially directed bore extending between each lumen of an elongated lead body having a plurality of internal longitudinally extending, circumferentially spaced lumina. The bores are located at longitudinally and circumferentially spaced locations and an elongated conductor cable is then drawn into and through each lumen of the lead body such that a terminal end thereof projects through and beyond an associated one of the bores. A metallic tube is slidably attached onto each conductor cable adjacent the cable's terminal end, then is firmly joined to its associated conductor cable. Thereupon, each metallic tube is affixed, as by welding, preferably, by laser welding, to an associated one of a plurality of tubular electrodes coaxial with, and overlying, the lead body at longitudinally spaced locations. In one instance, the tubular electrode may be a ring electrode with the lead body connected to a pacemaker. In another instance, the tubular electrode may be a shock coil electrode with the lead body connected to a defibrillator.

It has been a great challenge to electrically and reliably connect a small multi-strand conductor cable (for example: 0.006 inch cable consisting of 7 wires, in which the wire O.D is 0.002 inches) to a ring electrode or a multifilar shock coil electrode. Being of such small size, the connection is very difficult one to make and, once made, is very fragile and unlikely to endure for a multi-lumen lead body, where the cable is brought out from the inner lumen and attached to the electrode. The invention described herein, however, provides an easy, practical and reliable connection between such a small cable and an electrode on a multi-lumen lead body.

At the location of the electrode on the multi-lumen lead body, the cable end is drawn out from the inner lumen via a small pre-pierced hole on the multi-lumen insulation lead body tubing. A metallic tube is installed over the cable located outside the lead body. The metallic tube (such as Pt/Ir or MP35N) is crimped or compressed or otherwise operated upon to provide a permanent connection between the cable and the metallic tube. The ring electrode for a Brady lead or a shock coil electrode is then installed over the lead body and the crimped tube. Welding, and preferably laser welding, is used to provide permanent electrical connection between the electrode and the crimped tube.

A primary feature, then, of the present invention is the provision of an improved electrical lead for connecting an implantable medical device with selected body tissue to be stimulated by such device.

Another feature of the present invention is the provision of such an electrical lead which can be readily manufactured from commonly available materials.

Still another feature of the present invention is the provision of such an electrical lead which can be inexpensively manufactured while maintaining the performance achieved by much more expensive electrode designs.

Yet a further feature of the present invention is the provision of a technique for providing a secure electrical and mechanical connection between an elongated conductor cable and a mating electrode.

Still a further feature of the present invention is the provision of such an electrical lead constructed by drawing an elongated conductor cable first through each lumen of an elongated multi-lumen lead body, then into and through a generally radially directed bore extending between each lumen and the outer peripheral surface of the lead body, the generally radially directed bores being located at longitudinally spaced locations, such that a terminal end of the cable projects through, and beyond, an associated one of the generally radially directed bores, then slidably attaching a metallic tube onto each conductor cable adjacent its terminal end, then firmly joining each metallic tube and its associated conductor cable, and then affixing each metallic tube to an associated one of a plurality of tubular electrodes coaxial with, and overlying, the lead body at longitudinally spaced locations.

Yet another feature of the present invention is the provision of such an electrical lead wherein each electrode is affixed to its associated metallic tube by welding and, preferably, by laser welding.

Still another feature of the present invention is the provision of such an electrical lead wherein each tubular electrode is a ring electrode; and wherein the lead body is connected to a pacemaker.

Yet another feature of the present invention is the provision of such an electrical lead wherein each tubular electrode is a shock coil electrode and wherein the lead body is connected to a defibrillator.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 6 is a diagrammatic side elevation view, partly cut away and in section, illustrating a pacemaker lead embodying the invention;

FIG. 8 is a diagrammatic side elevation view, partly cut away and in section, illustrating a defibrillator lead embodying the invention.

DETAILED DESCRIPTIONS OF THE PREFERRED EMBODIMENTS

Figure 1:
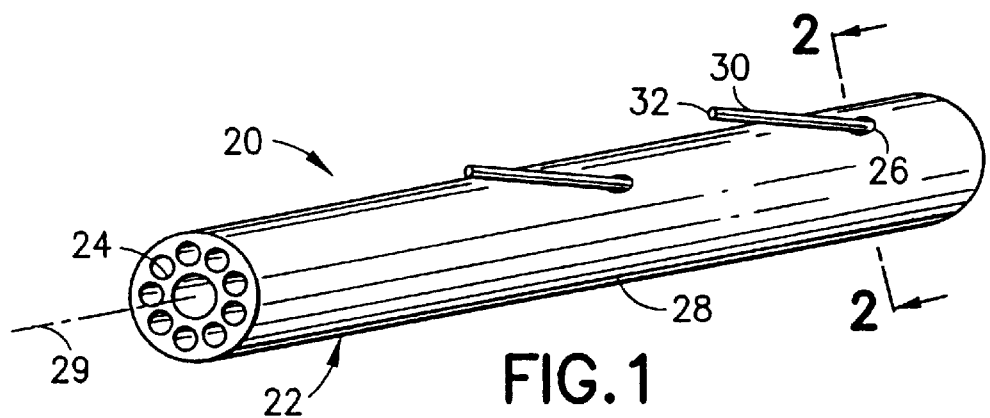
FIG. 1 is a perspective view of an implantable medical electrical lead embodying the present invention, at an interim stage of its construction.
Figure 2:
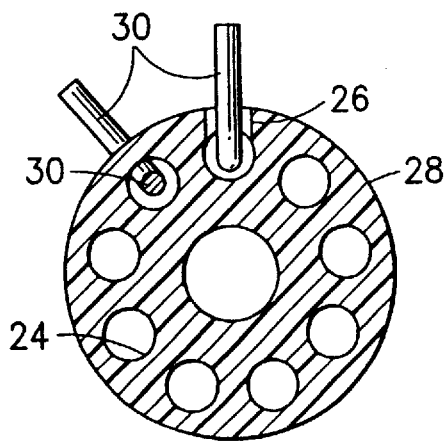
FIG. 2 is a cross-section view taken generally along line 2—2 in FIG. 1.

Turn now to the drawings and, initially, to FIGS. 1 and 2 which generally illustrate an implantable medical electrical lead 20 embodying the present invention. The lead 20 may be of the type designed for intravenous insertion for contact with the endocardium, and as such may be conventionally referred to as an endocardial lead. However, the invention need not be so limited. The lead 20 is provided with an elongated lead body 22 preferably fabricated of silicone rubber, polyurethane, or other suitable plastic material. The lead body has a plurality of internal longitudinally extending, circumferentially spaced lumina 24 and a plurality of generally radially directed bores 26 extending between each lumen and the outer peripheral surface 28 at longitudinally spaced locations. The lumina 24 are generally equally spaced circumferentially and are generally centered on an arc which has the same radial distance from a longitudinal axis 29 of the lead body 22.

Figure 3:
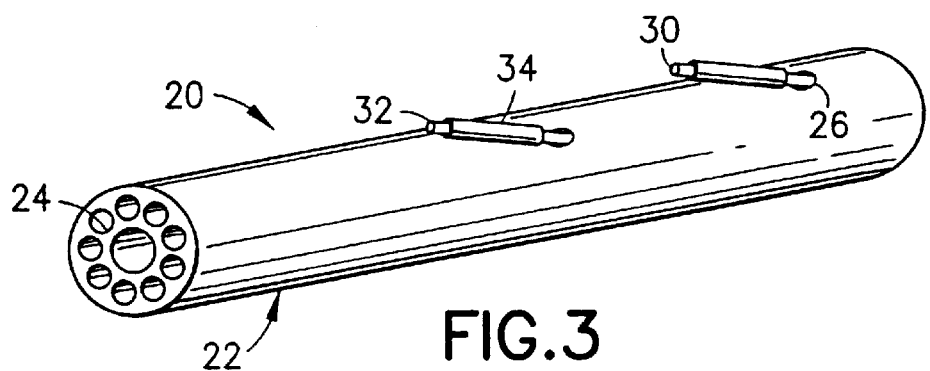
FIG. 3 is a perspective view of the implantable medical electrical lead of FIG. 1 but illustrating a subsequent stage of its construction.
Figure 4:
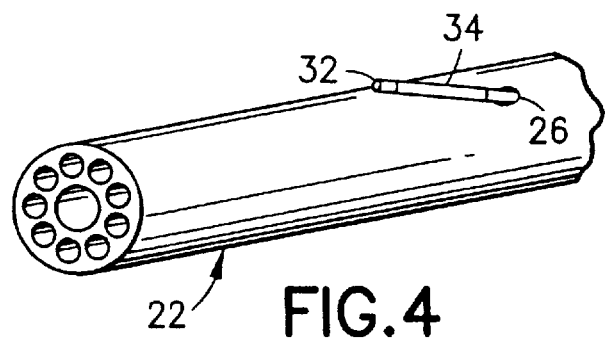
FIG. 4 is a perspective view of the implantable medical electrical lead of FIG. 1 but illustrating yet a further stage of its construction.

An elongated conductor cable 30 is received in and extends along each lumen 24 of the lead body 22 to a terminal end 32 which projects through and beyond an associated one of the generally radially directed bores 26. The conductor cable is typically of small multi-strand construction. It may be, for example, 0.006 inch diameter cable consisting of seven wires, in which the wire O.D is 0.002 inches. It may also be of a single strand or of more than seven strands. In any event, viewing FIG. 3, a metallic tube 34 is slidably applied to, or received on, each conductor cable 30 adjacent its terminal end 32 (see FIG. 3), then firmly joined (see FIG. 4) to the conductor cable. This step is preferably performed by crimping although it may be performed in some other suitable manner, by welding, for example. After the joint has been achieved, it is desirable to sever and remove any part of the cable 30 which extends beyond the crimped metallic tube 34.

Figure 5:
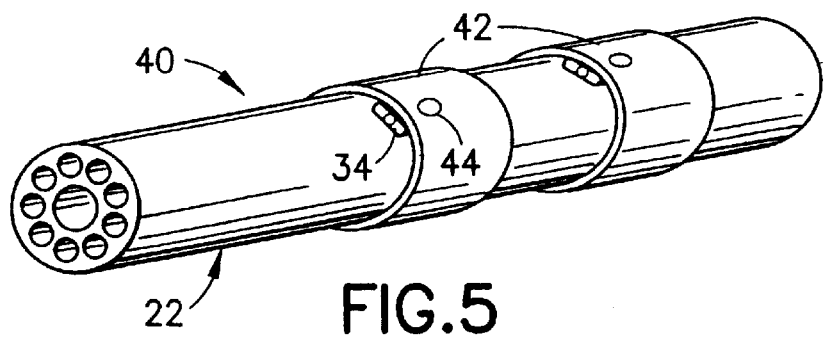
FIG. 5 is a perspective view of the implantable medical electrical lead of FIG. 1 but illustrating a final stage of its construction, being one embodiment of the invention.

A terminated electrical lead 40 is illustrated in FIG. 5 and depicts one embodiment of the invention. In this instance, a plurality of tubular, or ring, electrodes 42 are coaxial with, and overlie the lead body 22, specifically overlying each conductor cable 30 to which has been joined a metallic tube 34. Each electrode 42 is then affixed, as by welding and preferably, by laser welding, to an associated one of the metallic tubes 34. To this end, each electrode is formed with an aperture 44 through which a laser beam can be directed onto the metallic tube 34 underlying the electrode. The terminated electrical lead 40 is intended to be employed in conjunction with a pacemaker 46 (FIG. 6) to which it is suitably connected.

Figure 7:
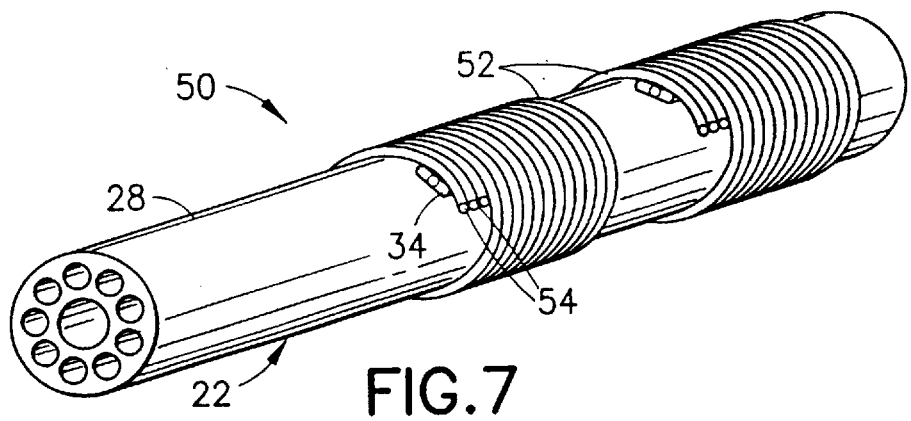
FIG. 7 is a perspective view of the implantable medical electrical lead of FIG. 1 but illustrating a final stage of its construction, being another embodiment of the invention.

A terminated electrical lead 50 is illustrated in FIG. 7 and depicts another embodiment of the invention. In this instance, a plurality of shock coil electrodes 52 are coaxial with, and overlie the lead body 22. As in the instance of the FIGS. 5 and 6 embodiment, each shock coil electrode 52 specifically overlies each conductor cable 30 to which has been joined a metallic tube 34. Each shock coil electrode 52 is then affixed, as by welding and preferably, by laser welding, to an associated one of the metallic tubes 34. In this embodiment, there is no equivalent to the aperture 44, since free ends 54 of the shock coil electrode 52 are openly exposed enabling the free manipulation of a laser beam so it can be directed onto the metallic tube 34 underlying the electrode. The terminated electrical lead 50 is intended to be employed in conjunction with a defibrillator 56 (FIG. 8) to which it is suitably connected.

Now that the construction of the invention has been presented, its significant advancement of the state of the art can be more fully appreciated. As the number of electrodes desired for a lead system increases, it is merely necessary to draw a fresh conductor cable 30 through a previously unused lumen 24, form an appropriately located bore 26, longitudinally spaced from existing bores 26, to connect the newly used lumen to the outer peripheral surface 28 of the lead body 22, then draw the terminal end 32 of the conductor cable through the bore and apply and join a metallic tube 34 to the conductor cable adjacent its terminal end. At this point, the appropriate electrode 42 or 52 is connected to the conductor cable as already described.

Figure 9:
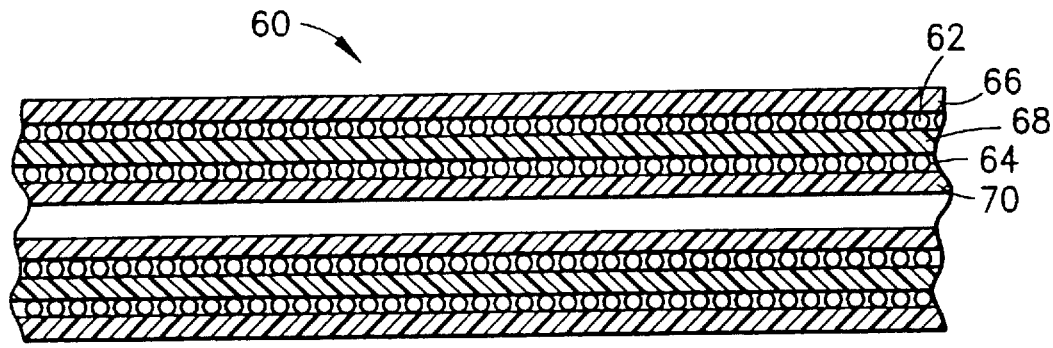
FIG. 9 is a side elevation view, in section, illustrating a prior art electrical lead.

What is particularly noteworthy is the fact that the diameter of the resultant electrical lead 20 never increases regardless of the number of electrodes to be terminated. This is in contrast to prior art constructions, as illustrated in FIG. 9. Such a known electrical lead 60 employs coiled conductors 62, 64, for example, to connect a pacemaker, defibrillator, or other pulse generating device to its associated electrode. The conductors 62, 64 are coaxial and are appropriately supported and separated by coaxial insulative tubing. Thus, each time there is an additional electrode to be terminated, the diameter of the electrical lead 60 necessarily increases to accommodate an additional conductor and an additional insulative tube. This is highly undesirable and is overcome by the invention presented above.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A method of making an implantable medical electrical lead, comprising the steps of:

(a) providing an elongated lead body having an internal longitudinally extending lumen, an outer peripheral surface, and a circumference;

(b) forming a generally radially directed bore extending between the lumen and the outer peripheral surface;

(c) drawing an elongated conductor cable into and through the lumen of the lead body such that a terminal end thereof projects through and beyond the generally radially directed bore;

(d) slidably attaching a metallic tube onto the conductor cable adjacent the terminal end thereof without enclosing the leadbody;

(e) firmly joining the metallic tube and the conductor cable; and (f) affixing the metallic tube to a tubular electrode coaxial with, and overlying, the lead body.

2. The method of making an implantable medical electrical lead, as set forth in claim 1, wherein the step (f) includes the step of:

affixing the electrode to the metallic tube by welding.

3. The method of making an implantable medical electrical lead, as set forth in claim 1, wherein the step (f) includes the step of:

affixing the electrode to the metallic tube by laser welding.

* * * * *